(12) United States Patent
Faini et al.

(10) Patent No.: US 9,963,465 B2
(45) Date of Patent: May 8, 2018

(54) METHOD OF FORMING METHYL PENAM DERIVATIVES

(71) Applicant: Allecra Therapeutics SAS, Saint Louis (FR)

(72) Inventors: Andrea Faini, Milan (IT); Marco Forzatti, Monza (IT); Giovanni Fogliato, Barzana (IT); Stefano Biondi, Pero (IT)

(73) Assignee: Allecra Therapeutics SAS, Saint Louis (FR)

( * ) Notice: Subject to any disclaimer, the term of this patent is extended or adjusted under 35 U.S.C. 154(b) by 0 days. days.

(21) Appl. No.: 15/311,146

(22) PCT Filed: May 14, 2015

(86) PCT No.: PCT/EP2015/060733
§ 371 (c)(1),
(2) Date: Nov. 14, 2016

(87) PCT Pub. No.: WO2015/173378
PCT Pub. Date: Nov. 19, 2015

(65) Prior Publication Data
US 2017/0101421 A1    Apr. 13, 2017

(30) Foreign Application Priority Data

May 15, 2014  (GB) .................................. 1408649.0

(51) Int. Cl.
*C07D 499/87*    (2006.01)
(52) U.S. Cl.
CPC ............ *C07D 499/87* (2013.01); *Y02P 20/55* (2015.11)
(58) Field of Classification Search
None
See application file for complete search history.

(56) References Cited

U.S. PATENT DOCUMENTS

2008/0015156 A1*  1/2008  Udayampalayam
                           Palanisamy .......... C07D 499/86
                                                          514/40

FOREIGN PATENT DOCUMENTS

WO    WO-2008/010048 A2    1/2008
WO    WO-2012/070071 A1    5/2012

OTHER PUBLICATIONS

Fisher et al., Bacterial resistance to beta-lactam antibiotics: compelling opportunism, compelling opportunity, Chem. Rev., 105(2):395-424 (2005).

International Search Report and Written Opinion, International Application No. PCT/EP2015/060733, dated Nov. 30, 2015.

Shapiro, Speculative strategies for new antibacterials: all roads should not lead to Rome, J. Antibiot (Tokyo), 66(7):371-86, Abstract Only (2013).

Watkins et al., Novel β-lactamase inhibitors: a therapeutic hope against the scourge of multidrug resistance, Front Microbiol., 4:392 (2013).

Lian Yu, "Amorphous pharmaceutical solids: preparation, characterization and stabilization", *Advanced Drug Delivery Reviews*, 48:27-42 (2001).

(Continued)

*Primary Examiner* — Deepak R Rao
*Assistant Examiner* — Laura M Daniel
(74) *Attorney, Agent, or Firm* — Marshall, Gerstein & Borun LLP

(57) ABSTRACT

A method of forming a compound of formula (IIIa):

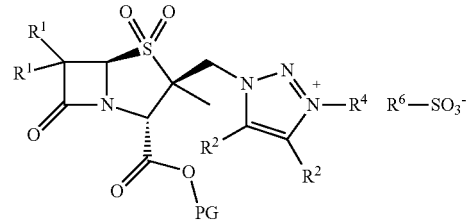

Formula (IIIa)

wherein: $R^1$ in each occurrence is independently selected from H, halogen, amino, $C_{1-5}$ alkyl, $C_{1-5}$ alkenyl and $C_{1-5}$ alkynyl; $R^2$ in each occurrence is independently selected from H, halogen, amino, $C_{1-5}$ alkyl, $C_{1-5}$ alkenyl and $C_{1-5}$ alkynyl; $R^4$ is $C_{1-5}$ alkyl; and $R^6$ is a $C_{1-5}$ fluoroalkyl; and PG is a protecting group, the method comprising the step of reacting a compound of formula (IIa) with a compound of formula (VIII):

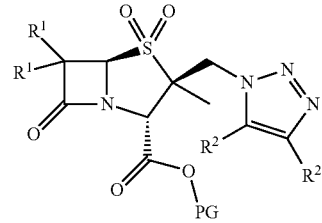

(IIa)

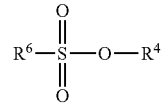

(VIII)

19 Claims, 4 Drawing Sheets

(56) References Cited

OTHER PUBLICATIONS

Stang et al., "Perfluoroalkanesulfonic Esters: Methods of Preparation and Applications in Organic Chemistry," Synthesis:85-126 (1982).
Written Opinion from the IP Office of Singapore for Singapore Patent Application No. 11201609494Y, dated Aug. 25, 2017.
Extended European Search Report for European Patent Application No. 17168966.4-1462, dated Jul. 7, 2017.
English Translation of Eurasian Office Action Application for Eurasian Patent Application No. 201692306, dated Jun. 21, 2017.

* cited by examiner

METHOD OF FORMING METHYL PENAM DERIVATIVES

CROSS REFERENCE TO RELATED APPLICATIONS

This is the U.S. national phase of PCT/EP2015/060733, filed May 14, 2015, which claims priority to Great Britain application no. 1408649.0 filed May 15, 2014, all of which are expressly incorporated herein by reference and made a part hereof.

FIELD OF THE INVENTION

The present invention relates to methods of forming methyl penam derivatives, in particular methyl penam derivatives suitable for use with β-lactam antibiotics as β-lactamase inhibitors.

BACKGROUND OF THE INVENTION

Emergence and dissemination of resistance is an inevitable consequence of the evolutionary dynamic set in motion by the introduction of antibiotics, irrespective of structural class or mode of action (Shapiro S. 2013. Speculative strategies for new antibacterials: all roads should not lead to Rome. J. Antibiot. 66: 371-386). Spread of resistance amongst clinically relevant pathogens has had an especially strong impact on the value of β-lactam antibiotics, heretofore regarded as very safe and efficacious therapies for serious bacterial infections. The appearance of new and aggressive β-lactamases, particularly extended spectrum β-lactamases (ESBLs) and other class A enzymes, has compromised the ability of β-lactams to combat infections, highlighting the need for development of new products (Fisher J F, Meroueh S O, Mobashery S. 2005. Bacterial resistance to β-lactam antibiotics: compelling opportunism, compelling opportunity. Chem. Rev. 105: 395-424). Whilst several β-lactamase inhibitors, which protect β-lactam antibiotics from hydrolysis, have been used in combination with some β-lactams, the capability of these β-lactamase inhibitors to preserve the antibacterial activity of β-lactams has eroded severely during the past decade, necessitating the search for new, more potent β-lactamase inhibitors to restore therapeutic utility of their β-lactam partners (Watkins R R, Papp-Wallace K M, Drawz S M, Bonomo R A. 2013. Novel β-lactamase inhibitors: a therapeutic hope against the scourge of multidrug resistance. Front. Microbiol. 4: 392).

WO 2008/010048 discloses β-lactamase inhibitors having the following formula:

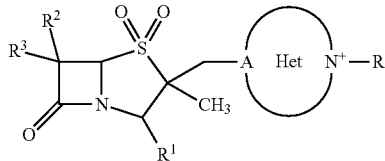

The β-lactamase inhibitors disclosed in WO 2008/010048 includes the compound (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide (formula A):

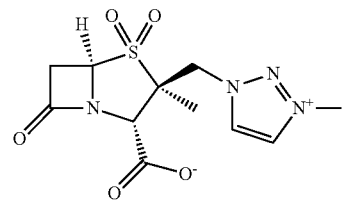

The R group is formed by a substitution reaction, for example by reaction with methyl iodide in the case of formula (A).

WO 2008/010048 discloses formation of amorphous compounds isolated by filtering and lyophilisation.

It is an object of the invention to provide an improved process for manufacture of 2-methyl penam derivatives.

It is a further object of the invention to provide a process for manufacture of 2-methyl penam derivatives that is suitable for industrial-scale manufacture.

SUMMARY OF THE INVENTION

In a first aspect the invention provides a method of forming a compound of formula (IIIa):

Formula (IIIa)

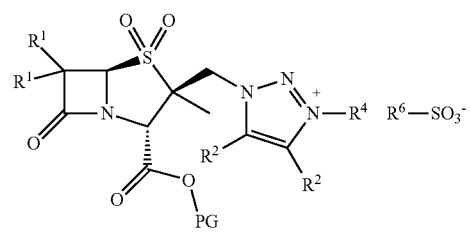

wherein:
$R^1$ in each occurrence is independently selected from H, halogen, amino, $C_{1-5}$ alkyl, $C_{1-5}$ alkenyl and $C_{1-5}$ alkynyl;
$R^2$ in each occurrence is independently selected from H, halogen, amino, $C_{1-5}$ alkyl, $C_{1-5}$ alkenyl and $C_{1-5}$ alkynyl;
$R^4$ is $C_{1-5}$ alkyl; and
$R^6$ is a $C_{1-5}$ fluoroalkyl; and
PG is a protecting group,
the method comprising the step of reacting a compound of formula (IIa) with a compound of formula (VIII):

(IIa)

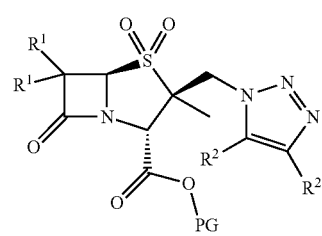

(VIII)

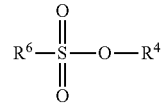

In a second aspect the invention provides a method of forming a compound of formula (IV):

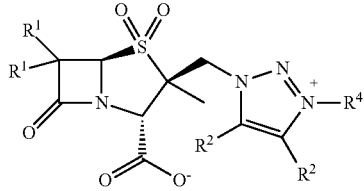
(IV)

wherein $R^1$ in each occurrence is independently selected from H, halogen, amino, $C_{1-5}$ alkyl, $C_{1-5}$ alkenyl and $C_{1-5}$ alkynyl; $R^2$ in each occurrence is independently selected from H, halogen, amino, $C_{1-5}$ alkyl, $C_{1-5}$ alkenyl and $C_{1-5}$ alkynyl; and $R^4$ is $C_{1-5}$ alkyl;

the method comprising the step of reacting a compound of formula (III) with a 2-ethylhexanoate salt:

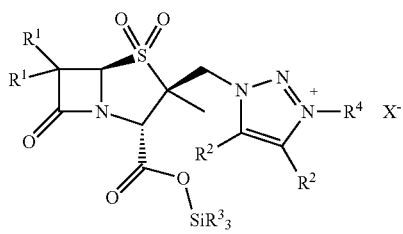
(III)

wherein X— is an anion and each $R^3$ is independently selected from the group consisting of $C_{1-10}$ hydrocarbyl and $C_{1-5}$ alkoxy.

The compound of formula (III) reacted in the second aspect of the invention may be formed by the method described in the first aspect in the case where PG of formula (IIIa) is a group of formula $SiR^3{}_3$.

In a third aspect the invention provides a method of forming a compound of formula (II):

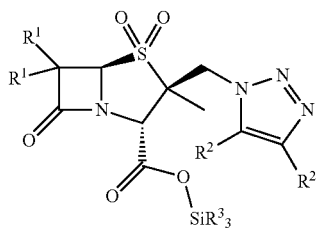
(II)

wherein $R^1$ in each occurrence is independently selected from H, halogen, amino, $C_{1-5}$ alkyl, $C_{1-5}$ alkenyl and $C_{1-5}$ alkynyl; $R^2$ in each occurrence is independently selected from H, halogen, amino, $C_{1-5}$ alkyl, $C_{1-5}$ alkenyl and $C_{1-5}$ alkynyl; and $R^3$ in each occurrence is independently selected from the group consisting of $C_{1-5}$ alkoxy and $C_{1-10}$ hydrocarbyl, optionally $C_{1-5}$ alkoxy, $C_{1-5}$ alkyl, phenyl, and phenyl-$C_{1-4}$ alkyl;

the method comprising the step of reacting a compound of formula (I) with less than a molar equivalent of a compound of formula (V)

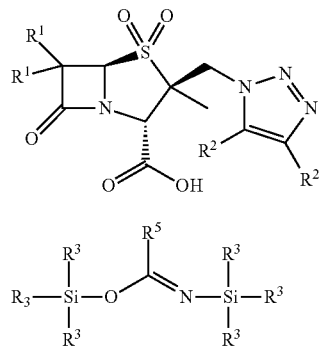
(I)

(V)

wherein $R^5$ is $C_{1-5}$ alkyl.

The compound of formula (II) formed by the method of the third aspect may be used in the reaction of the first aspect in the case where PG of formula (IIa) is a group of formula $SiR^3{}_3$.

DESCRIPTION OF THE DRAWINGS

The invention will now be described in more detail with reference to the Figures in which.

DETAILED DESCRIPTION OF THE INVENTION

Figure 1:
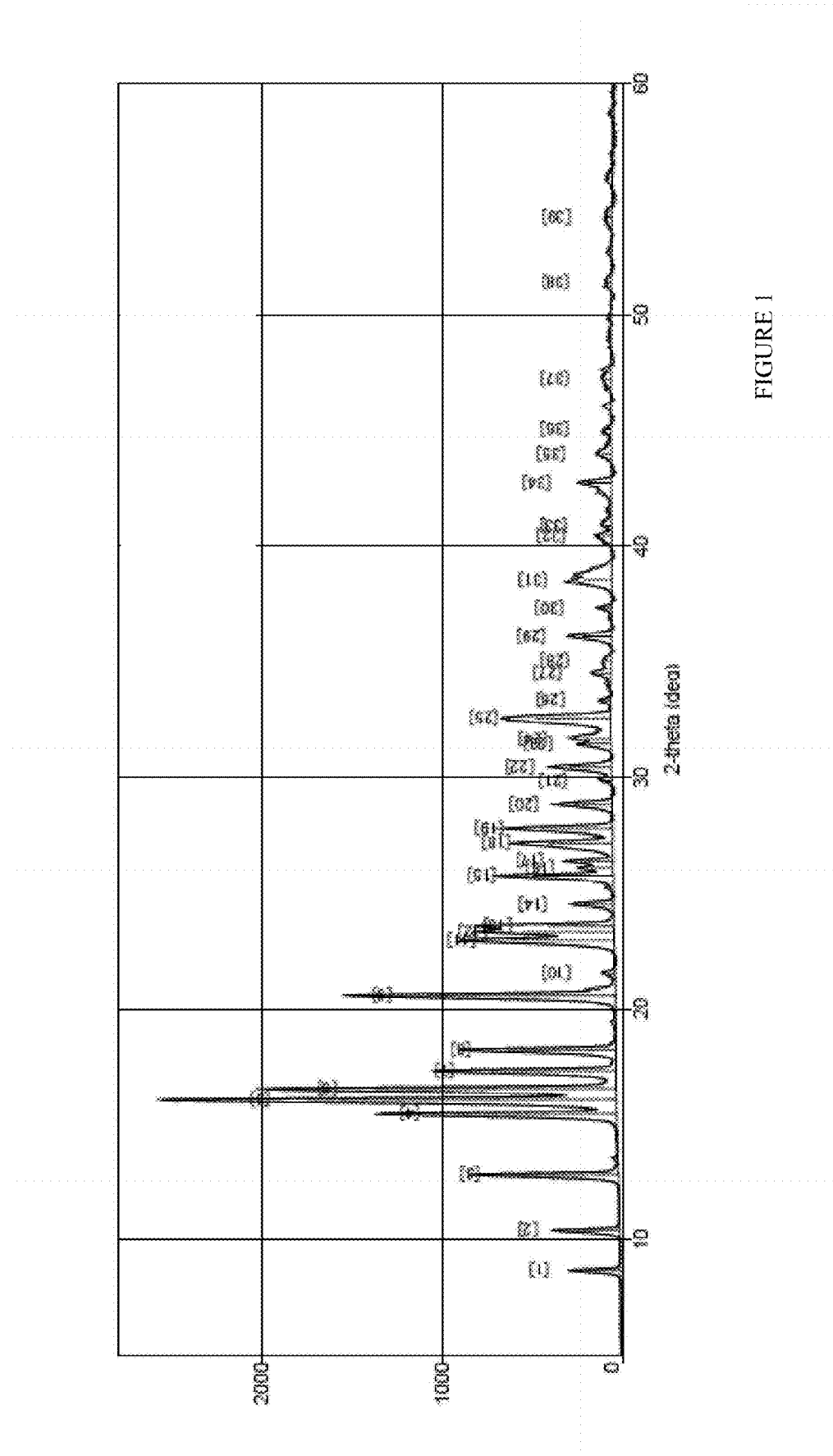
FIG. 1 is an XRPD spectrum of a crystalline compound prepared by a process according to an embodiment of the invention.

A process for preparing a compound of formula (IV) is illustrated in Scheme 1.

Scheme 1

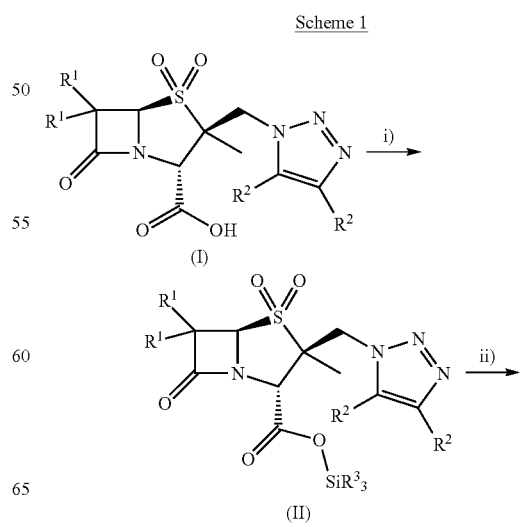

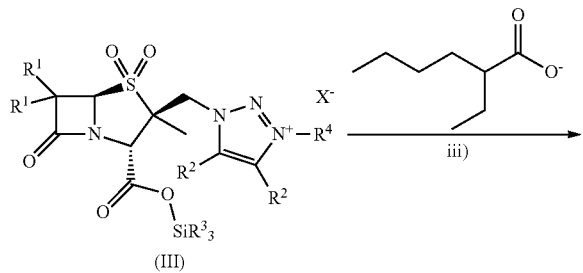

(III)

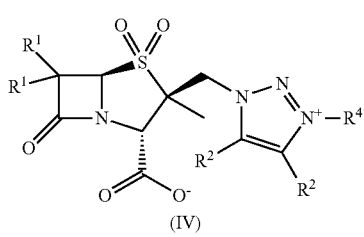

(IV)

wherein:
R¹ in each occurrence is independently selected from H, halogen, amino, $C_{1-5}$ alkyl, $C_{1-5}$ alkenyl and $C_{1-5}$ alkynyl;
R² in each occurrence is independently selected from H, halogen, amino, $C_{1-5}$ alkyl, $C_{1-5}$ alkenyl and $C_{1-5}$ alkynyl;
R³ in each occurrence is independently selected from $C_{1-10}$ hydrocarbyl and $C_{1-5}$ alkoxy, optionally $C_{1-5}$ alkyl, $C_{1-5}$ alkoxy, phenyl, and phenyl-$C_{1-4}$ alkyl;
R⁴ is $C_{1-5}$ alkyl; and
X is an anion.
Preferably, each R¹ is H.
Preferably, each R² is H.
Preferably, R⁴ is methyl.
Each of steps (i)-(iii) will now be described in more detail.
Step (I): Silylation
The carboxyl group of the compound of formula (I) is silylated in step (i). Preferably, silylation is carried out using an amide of formula (V):

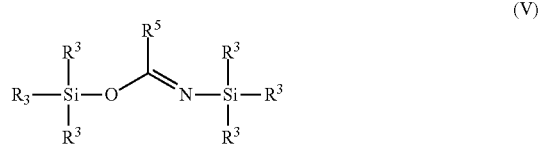

(V)

wherein R³ in each occurrence is independently selected from $C_{1-10}$ hydrocarbyl or $C_{1-5}$ alkoxy, optionally $C_{1-5}$ alkyl, $C_{1-5}$ alkoxy, phenyl, and phenyl-$C_{1-4}$ alkyl, and R⁵ is selected from $C_{1-5}$ alkyl.
Preferably, each R³ is methyl. Preferably, each R⁵ is methyl.
A preferred compound of formula (V) is N,O-bis trimethylsilylacetamide.
The reaction may be carried out in a polar aprotic solvent, optionally a chlorinated solvent such as dichloromethane.
The compound of formula (I) may be reacted with at least a molar equivalent of the compound of formula (V), optionally a molar excess of the compound of formula (V).

However, the present inventors have surprisingly found that both of the silyl groups of the compound of formula (V) may be utilized in silylation of the compound of formula (I).
Accordingly, in a preferred embodiment the compound of formula (I) is reacted with less than a molar equivalent of the compound of formula (V), optionally no more than 0.9 molar equivalents, optionally no more than 0.8, 0.7 or 0.6 molar equivalents.
The compound of formula (V) may be added to the reaction mixture in a single addition or may be added in two or more portions.

Step (II): Alkylation

The alkylation of step (ii) may be a $C_{1-5}$ alkylation, preferably a methylation.
Alkylation may be carried out with any suitable alkylating group, preferably a compound of formula (VI):

R⁴—X (VI)

Wherein R⁴ is a $C_{1-5}$ alkyl group and X is a leaving group. Preferably, R⁴ is methyl.
Optionally, X is selected from the group consisting of chloride, bromide, iodide, and sulfonates.
Exemplary sulfonates are groups of formula (VII):

(VII)

wherein R⁶ is selected from aryl, optionally phenyl, that may be unsubstituted or substituted with one or more substituents, and $C_{1-5}$ alkyl wherein one or more H atoms of the $C_{1-5}$ alkyl group may be replaced with F, and * represents a bond to R¹. Exemplary groups of formula (VII) include trifluoromethanesulfonate (triflate) and p-toluenesulfonate (tosylate).
Preferably, wherein R⁶ is $C_{1-5}$ alkyl wherein one or more H atoms of the $C_{1-5}$ alkyl group are replaced with F. More preferably, R⁶ is trifluoromethyl.
The reaction may be carried out any temperature up to the boiling point of the reaction mixture at atmospheric pressure. Surprisingly, the present inventors have found that use of a fluorinated alkyl R⁶ may allow the alkylation step to proceed at low temperature, optionally at a temperature of less than 20° C., optionally less than 10° C., optionally at about 0° C. The present inventors have further found that use of a fluorinated alkyl R⁶ allows for a significantly faster reaction than use of halogen groups R⁶.
By use of a low temperature reaction using a fluorinated alkyl R⁶, evaporation of volatile alkylating agents, for example methyl iodide, may be reduced or eliminated.
Preferably, the silylated compound formed in step (i) is not isolated before the alkylation step. Compounds (II) and (III) of Scheme 1 carry a silyl protecting group protecting the carboxyl group of these compounds, however it will be appreciated that the protecting group for reaction step (ii) may be another protecting group PG. The skilled person will be aware of other protecting groups suitable for protecting the carboxyl group of compounds of formula (II) during the alkylation of step (ii). Exemplary protecting groups PG other than the group of formula $SiR^3_3$ include allyl, which may be removed following alkylation using a metal 2-ethylhexanoate and Pd(0); groups which may be removed by hydrogenolysis, for example benzyl, benzidryl and p-nitrobenzyl; and groups that can be removed with a base, for example fluorenylmethyl. Further protecting groups for protection of a carboxyl are described in Theodora W. Greene and Peter G. M. Wuts, "Protective Groups in Organic Synthesis", Second Edition, John Wiley & Sons, Inc., the contents of which are incorporated herein by reference.

Step (III): Deprotection

The present inventors have found that the silyl group of the compound of formula (III) may be removed by treatment with 2-ethylhexanoates to yield a solid product, and treatment with a 2-ethylhexanoate can yield crystals of the compound of formula (IV). This is surprising because the present inventors have found that treatment with methanol, ethanol or isopropanol or the bases sodium hydroxide or sodium acetate yields a non-solid product, such as an oil, a gum or a gel, that cannot be readily be converted to a solid form.

Exemplary 2-ethylhexanoates are metal 2-ethylhexanoates. Suitable metals include alkali and alkali earth metals, for example lithium, sodium, potassium, calcium and magnesium.

Preferably, the compound of formula (III) is not isolated before the desilylation step.

The compound of formula (III) may be added to a solution of a metal 2-ethylhexanoate to produce crystals of the compound of formula (IV). Exemplary solvents for the solution are alcohols, preferably ethanol.

Crystallisation

The compound of formula (IV) may be amorphous or crystalline. Crystalline compounds of formula (IV) may be easier to handle and more stable than amorphous compounds.

Methods of forming crystalline compounds of formula (IV) include, without limitation, dissolving or dispersing an amorphous compound of formula (IV) in a solvent or solvent mixture and inducing formation of crystals by adding one or more antisolvents to the solution or dispersion; cooling the solution or dispersion; and/or adding a crystal of a compound of formula (IV) to provide a nucleation point for crystallisation. An "antisolvent" as used herein means a liquid in which the compound of formula (IV) has a lower solubility than a solvent of the solution or dispersion that the antisolvent is added to.

Methods of crystallisation are described in GB 1319776.9, the contents of which are incorporated herein by reference.

Applications

Compounds of formula (IV) may be used in a pharmaceutical composition with one or more antibiotics, and may comprise one or more conventional pharmaceutically acceptable excipient(s).

Compounds of formula (IV) may be administered in a composition with an antibiotic, or an antibiotic and a compound of formula (IV) may be administered separately.

A pharmaceutical composition as described herein may be in an injectable form for intravenous injection. The composition may contain stabilizing agents. The composition may be in suitable sterile solid form ready for reconstitution to form an injectable solution, for example a saline solution.

Exemplary antibiotics are β-lactam antibiotics, in particular penicillins and cephalosporins and may be selected from Amoxicillin, Ampicillin, Apalcillin, Azlocillin, Bacampicillin, Carbenacillin, Cloxacillin, Dicloxacillin, Flucloxacillin, Lenampicillin, Mecillinam, Methacillin, Mezlocillin, Nafcillin, Oxacillin, Penicillin G, Penicillin V, Piperacillin, Temocillin, Ticarcillin, Aztreonam, BAL30072, Carumonam, PTX2416, Tigemonam, Cefaclor, Cefadroxil, Cefalexin, Cefalotin, Cefamandole, Cefapirin, Cefazolin, Cefbuperazone, Cefdinir, Cefepime, Cefetamet, Cefixime, Cefmenoxime, Cefmetazole, Cefminox, Cefonicid, Cefoperazone, Cefotaxime, Cefotetan, Cefotiam, Ceftiofur, Cefovecin, Cefoxtin, Cefpodoxime, Cefprozil, Cefquinome, Cefradine, Cefminox, Cefsulodin, Ceftaroline, Ceftazidime, Ceftezole, Ceftibuten, Ceftizoxime, Ceftobiprole, Ceftolozane, Ceftriaxone, Cefuroxime, Cefuzoname, Cephalexin, Cephalotin, Flomoxef, Latamoxef, Loracarbef Imipenem, Meropenem, Doripenem, Ertapenem, Biapenem, Panipenem, Faropenem or derivatives thereof.

The antibiotic may be selected from aminoglycosides: Amikacin, Arbekacin, Apramycin, Dibekacin, Gentamicin, Isepamicin, Kanamycin, Neomycin, Netilmicin, Plazomicin, Sisomicin, Spectinomyin, Streptomycin, Tobramycin or derivatives thereof.

The antibiotic may be selected from quinolones: Cinoxacin, Ciprofloxacin, Enofloxacin, Gatifloxacin, Gemifloxacin, Levofloxacin, Moxifloxacin, Nalidixic acid, Norfloxacin, Oxafloxacin, or derivatives thereof.

The antibiotic may be selected from antimicrobial peptides, for example Colistin, Polymyxin B or derivatives thereof.

A pharmaceutical composition as described herein may comprise only one or more than one antibiotic.

A pharmaceutical composition containing a crystalline compound of formula (I) may contain or be co-administered with bactericidal or permeability-increasing-g protein product (BPI) or efflux pump inhibitors to improve activity against gram negative bacteria and bacteria resistant to antimicrobial agents. Antiviral, antiparasitic, antifungal agents may also be administered in combination with the inhibitor compounds.

The pharmaceutical composition may contain complexing agents or anticoagulants, antioxidants, stabilizers, aminoglycosides, pharmaceutically acceptable salts or the like or mixtures thereof.

In particular the pharmaceutical composition may contain □-lactam antibiotics, preferably penicillins, cephalosporins, carbapenem, monobactams, more preferably piperacillin, cefepime; ceftriaxone; meropenem, aztreonam.

The pharmaceutical composition may contain buffers, for example sodium citrate, sodium acetate, sodium tartrate, sodium carbonate, sodium bicarbonate, morpholinopropanesulfonic acid, other phosphate buffers and the like and chelating agents like ethylenediaminetetraacetic acid (EDTA), diethylenetriaminepentaacetic acid, hydroxyethylenediaminetriacetic acid, nitrilotriacetic acid, 1,2-diaminocyclohexanetetraacetic acid, bis(2-aminoethyl)ethyleneglycoltetraacetic acid, 1,6-hexamethylenediaminetetraacetic acid and the like or pharmaceutically acceptable salts thereof.

A pharmaceutical composition as described herein may be administered to a human or warm-blooded animal by any suitable method, and preferably by intravenous injection.

EXAMPLES

Synthesis of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide (4)

Compound (4) was prepared according to Scheme 2.

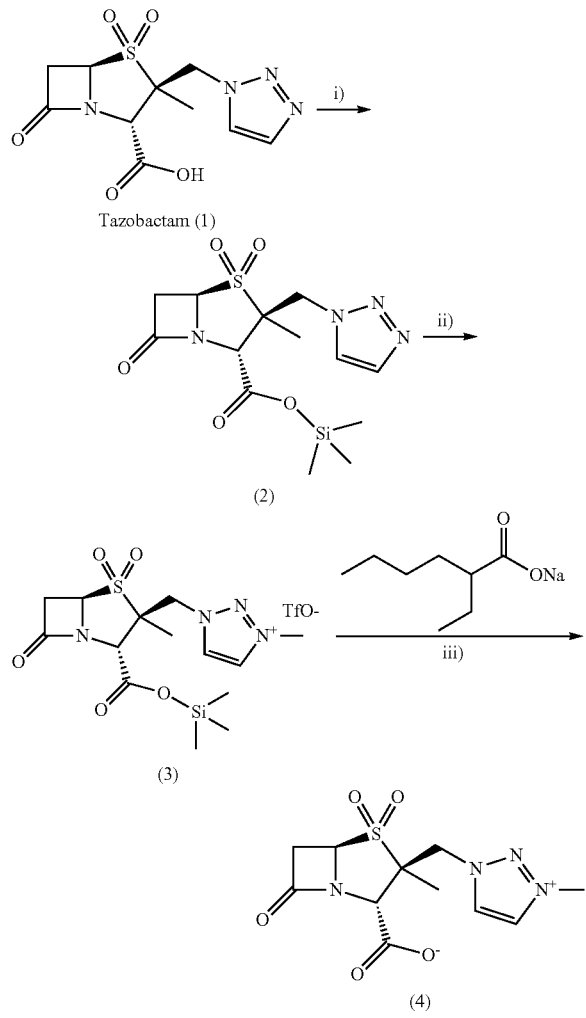

i) N,O-bis-trimethylsilylacetamide, CH$_2$Cl$_2$; ii) CH$_3$OTf; iii) Na 2-ethylhexanoate In a round bottom flask under nitrogen flow 100 g of Tazobactam acid (1) and 500 mL of Dichloromethane are loaded. The temperature is adjusted to +30/35° C. then 37 g of N,O-Bis(trimethylsilyl) acetamide are loaded in 15-20 minutes maintaining the temperature to +35/42° C. The mixture is heated to reflux (+40/42° C.) for 60 minutes. If the solution is not clear, N,O-Bis(trimethylsilyl) acetamide is loaded in small portions (0.5-1.0 g each) waiting 15 minutes every time till a clear solution containing intermediate (2) is obtained. 0.55 moles of N,O-Bis(trimethylsilyl) acetamide is used, with further 0.1-0.2 equivalents being added if the reaction is not complete.

Then the temperature is cooled down to 0/+5° C. and 70 g of Methyl trifluoromethanesulfonate are loaded in 60-90 minutes maintaining the temperature at 0/+5° C. After 30 minutes the reaction is monitored by HPLC to control the disappearance of intermediate (2) and formation of intermediate (3). The reaction is monitored every 30 minutes until completion.

In a round bottom flask, under nitrogen, are loaded 500 mL of Ethanol and 55 g of Sodium 2-Ethylhexanoate and the temperature is adjusted to +20/25° C., then the reaction solution containing intermediate (3) is added in 60-90 minutes maintaining the temperature of +20/25° C. under vigorous stirring. The suspension is stirred for 30 minutes then is filtered and washed with 300 mL of Ethanol followed by 500 mL of Dichloromethane under nitrogen. The crude product (4) is dried under nitrogen flow till constant weight (150 g) is obtained. The crude product compound (4) was isolated as a solid product (HPLC assay=70%, yield=80%).

Purification of (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide (4)

In a round bottom flask 800 mL of Dimethylformamide are loaded, the temperature is adjusted to +20/25° C. then crude Compound 4 (150 g) obtained above is loaded using 100 mL of Dimethylformamide to facilitate the transfer. The mixture is stirred for 5 minutes and a solution is obtained, then and after a few minutes crystallization takes place. The suspension is stirred for about 3 hours, then is cooled to 0/+5° C. and stirred for another 3 hours.

The solid is filtered and washed with 300 mL of Dimethylformamide pre-cooled to 0/+5° C. Compound 4 is then suspended in 700 mL of Ethyl acetate and the temperature is adjusted to +40/45° C. The suspension is stirred for 30 minutes then the solid is filtered and washed with 150 mL of Ethyl acetate pre-heated to +40/45° C. The suspension with Ethyl acetate is repeated twice. Finally Compound 4 is dried under vacuum at +40° C. till constant weight is achieved (66 g, HPLC assay=99%, yield=76%).

Compound 4 Sterile Filtration and Recrystallization Procedure

In a round bottom flask 350 mL of Methanol are loaded, the temperature is adjusted to +30/35° C. then 100 g of Compound 4 are loaded and finally the flask is washed with 60 mL of Methanol. After 5-10 minutes a solution is obtained. The solution is diluted with 330 mL of acetone adjusting the temperature to +20/+25° C. The obtained solution is treated with 2.2 g of charcoal for 20 minutes then filtered using a 0.22 microM filter and the filter is washed with a mixture of 13 mL of Methanol and 110 mL of Acetone. The temperature of the solution is adjusted to +30/35° C. and under vigorous stirring 830 mL of Acetone are loaded in about 15-20 minutes. After stirring for 60 minutes at temperature of +30/35° C. 1170 mL of Acetone are loaded in 45-60 minutes. Then the temperature is adjusted to +20/25° C. in about 30-60 minutes and maintained for 30 minutes. The obtained crystalline solid is filtered and washed with 430 mL of Acetone. Finally the product is dried under vacuum at +40° C. till constant weight is achieved (83 g of Compound 4) are obtained with an HPLC assay=98-99%, yield=t 80%).

FIG. 1 is an XRPD spectrum of crystalline Compound (4) acquired in transmission mode on a Rigaku MiniFlex 600 using the following conditions:

| | |
|---|---|
| X Ray | 40K Volt, 15 mA |
| Wavelength | CuKalfa => lambda 1.541862A |
| Scan axis | Theta/2-Theta |
| Scan range | 5.0000-60.0000 deg |
| Time acquisition | 60 min |

Figure 2:
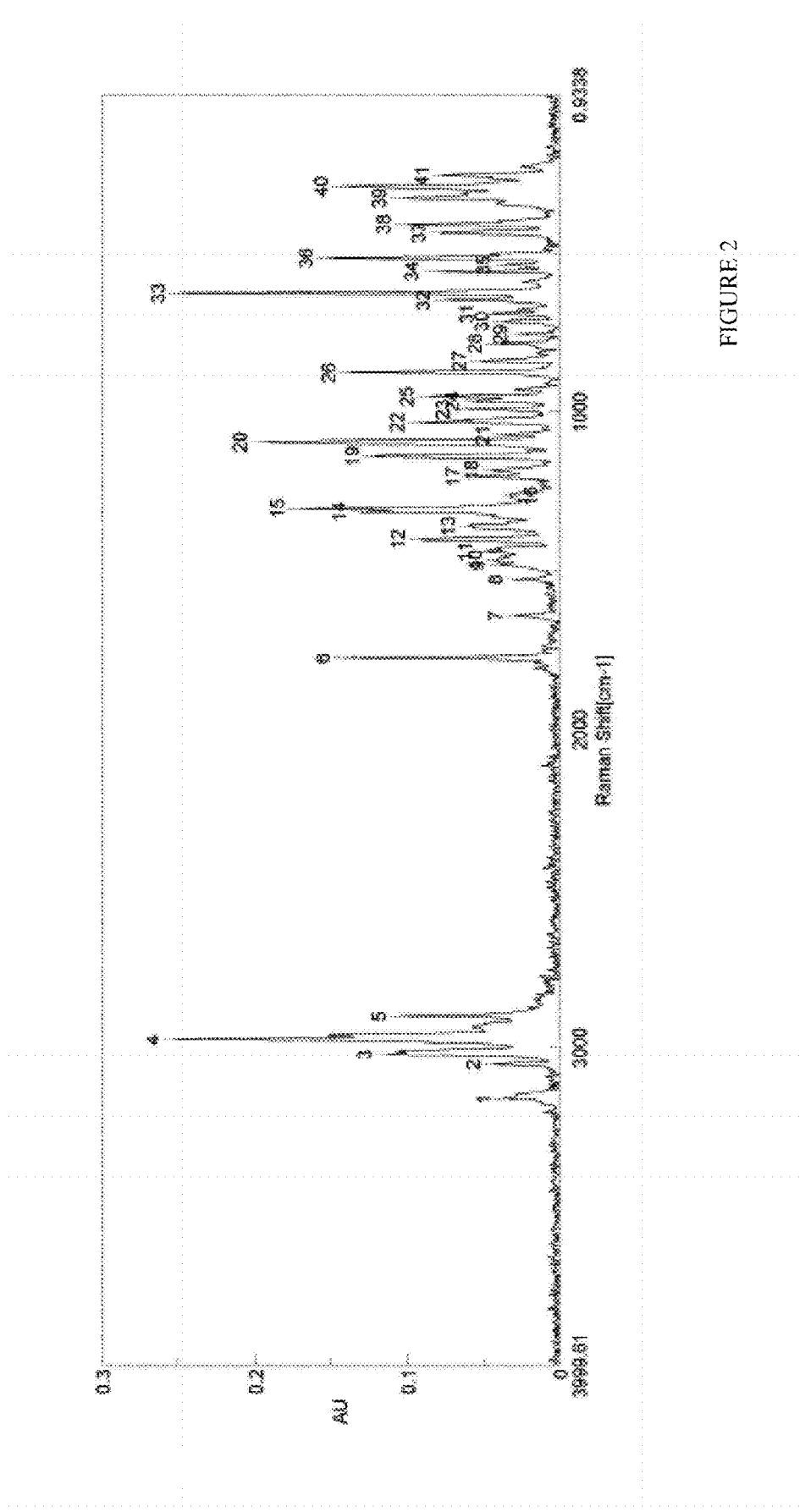
FIG. 2 is a Raman spectrum of a crystalline crystalline compound prepared by a process according to an embodiment of the invention.

FIG. 2 is a Raman spectrum of crystalline Compound (4) run on a Jasco RFT-600: light source: Nd-YAG (1064 nm: exciting wavelength).

Figure 3:
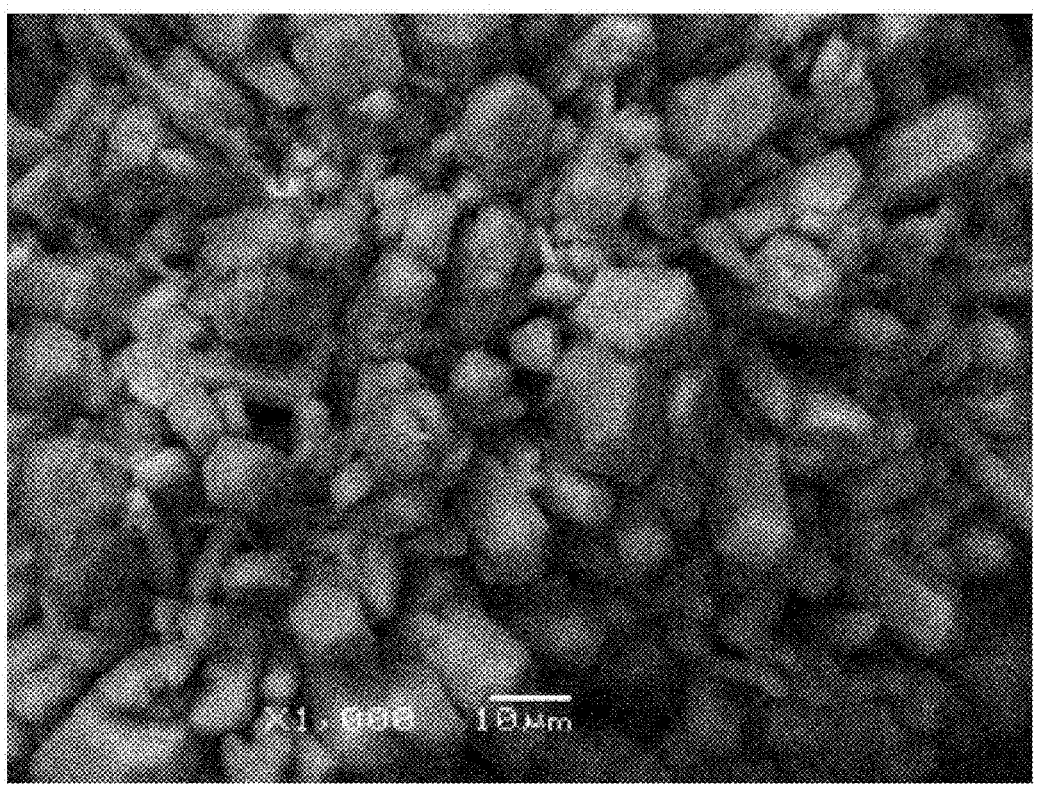
FIG. 3 is a scanning electron microscope image of a crystalline crystalline compound prepared by a process according to an embodiment of the invention.

FIG. 3 is a scanning electron microscope image of crystalline Compound (4) using a JEOL JSM 5500 LV scanning electron microscope, operating at 30 kV in low vacuum (30 Pa) with the backscattered electron technique.

Comparative Example 1

Silylation step (i) of Scheme 2 was performed using varying molar ratios of the silylating agent N,O-bis trimethylsilylacetamide (BSA).

Figure 4:
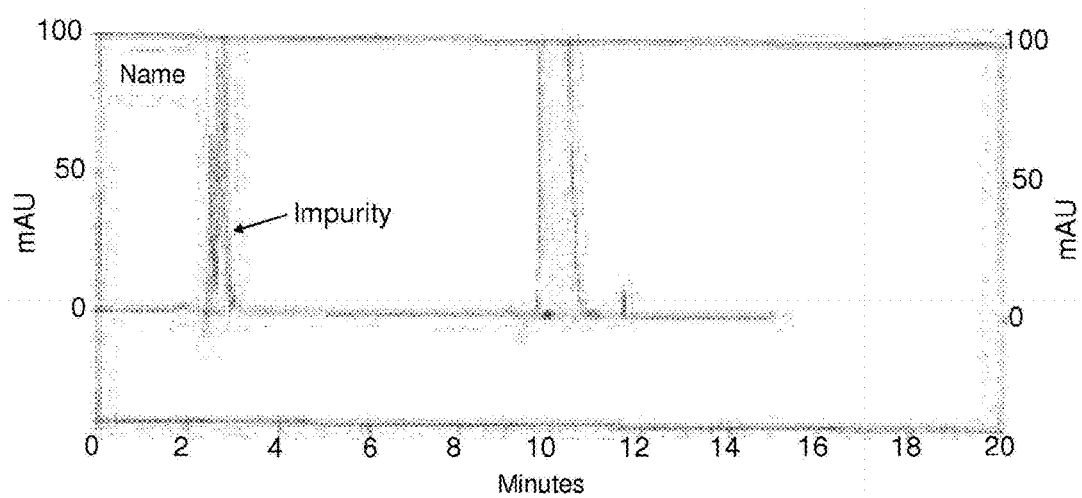
FIG. 4 is a LCMS spectrum of the product of a reaction between (2S,3S,5R)-3-methyl-3-((3-methyl-1H-1,2,3-triazol-3-ium-1-yl)methyl)-7-oxo-4-thia-1-azabicyclo[3.2.0]heptane-2-carboxylate 4,4-dioxide and N,O-bis trimethylsilylacetamide.

Silylation using 1.2 equivalents of BSA at 20-25 C as disclosed in WO 2008/010048 results in formation of an unidentified side-product, observable in LCMS as illustrated in FIG. 4.

With reference to Table 1, the quantity of this impurity can be greatly reduced by using a lower molar equivalent of BSA.

TABLE 1

| BSA equivalents | Temperature | Ratio % Impurity/silylated product |
|---|---|---|
| 1.2 | +30/35° C. | 24 |
| 1.8 | 0/5° C. | 73 |
| 0.5 | +40/42° C. | 1.5 |

Comparative Example 2

Methylation step (ii) of Scheme 2 was performed using iodomethane, as disclosed in WO 2008/010048 and methyl tosylate. With reference to Table 2, reactions using methyl triflate are much faster, provide a higher yield, can be conducted at much lower temperatures and require a smaller amount of methylating agent than either methyl tosylate or iodomethane. Furthermore, use of methyl triflate at relatively low temperature avoids safety issues arising from toxicity of methylating agents used at relatively high temperature, such as use of iodomethane at or above its boiling point.

TABLE 2

| Methylating agent | Solvent | Equivalents | Reaction time | Temperature | yield |
|---|---|---|---|---|---|
| Iodomethane | Acetone | 7.2 | 22 h | +45/48° C. | 44.3% |
| MeOTs | Acetone | 7.2 | 25 h | +45/48° C. | 54.1% |
| MeOTf | Acetone | 1.4 | 30 min. | 0/+5° C. | 98.0% |
| MeOTf | Acetone | 1.4 | 30 min. | +10/15° C. | 68.0% |
| MeOTf | THF | 1.4 | 30 min. | +15/20° C. | 67.0% |
| MeOTf | $CH_2Cl_2$ | 1.4 | 30 min. | 0/+5° C. | 98.0% |

Comparative Example 3

Desilylation step (iii) of Scheme 2 was attempted using a range of alcohols such as methanol, ethanol and 2-propanol. This approach led to recovery of product in form of oil or gel. These oils or gel were treated with different solvents such ACN, THF and Acetone, which gave complete dissolution and no solid material could be recovered. Use of diethyl ether, toluene, hexane and, heptane led to other gels and no solid could be recovered. Bases were tried to adjust pH to neutrality. For this purpose NaOH solution, AcONa (as is and in aqueous and organic solutions) and Sodium-2-ethylhexanoate (as is or in organic solutions) were tested. The use of sodium hydroxide in aqueous solution led to gel and gummy product. AcONa as is did not originate precipitation of any solid. A solid material containing Compound 4 was obtained using a mixture of sodium-2-ethylhexanoate and ethanol as described in the Example above.

Although the present invention has been described in terms of specific exemplary embodiments, it will be appreciated that various modifications, alterations and/or combinations of features disclosed herein will be apparent to those skilled in the art without departing from the scope of the invention as set forth in the following claims.

The invention claimed is:

1. A method of forming a compound of formula (IIIa):

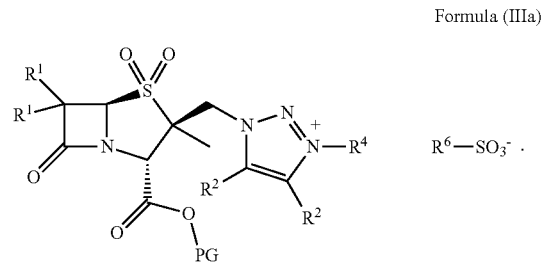

Formula (IIIa)

wherein:
R$^1$ in each occurrence is independently selected from H, halogen, amino, $C_{1-5}$ alkyl, $C_{2-5}$ alkenyl and $C_{2-5}$ alkynyl;
R$^2$ in each occurrence is independently selected from H, halogen, amino, $C_{1-5}$ alkyl, $C_{2-5}$ alkenyl and $C_{2-5}$ alkynyl;
R$^4$ is $C_{1-5}$ alkyl; and
R$^6$ is a $C_{1-5}$ fluoroalkyl; and
PG is a protecting group,
the method comprising the step of reacting a compound of formula (IIa) with a compound of formula (VIII):

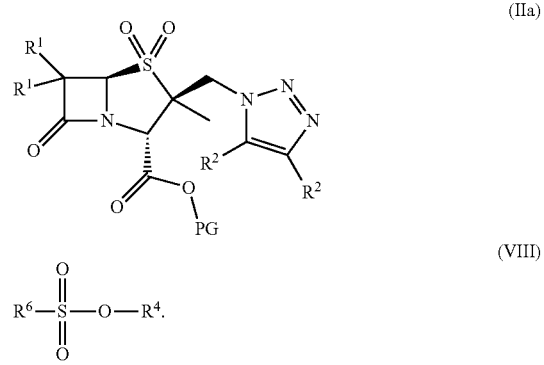

2. A method according to claim 1 wherein PG is a group of formula SiR$^3{}_3$ wherein R$^3$ in each occurrence is independently selected from $C_{1-10}$ hydrocarbyl or $C_{1-5}$ alkoxy.

3. A method according to claim 1 wherein $R^4$ is methyl.

4. A method according to claim 1 wherein $R^6$ is a $C_{1-5}$ perfluoroalkyl.

5. A method according to claim 4 wherein $R^6$ is trifluoromethyl.

6. A method according to claim 1 wherein the reaction is performed in a polar, aprotic solvent.

7. A method according to claim 1 wherein the reaction is performed at a temperature of no more than 10° C.

8. A method of forming a compound of formula (IV):

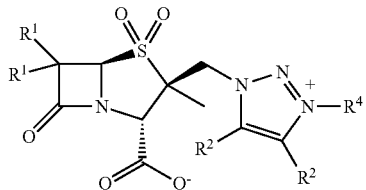

(IV)

wherein $R^1$ in each occurrence is independently selected from H, halogen, amino, $C_{1-5}$ alkyl, $C_{2-5}$ alkenyl and $C_{2-5}$ alkynyl; $R^2$ in each occurrence is independently selected from H, halogen, amino, $C_{1-5}$ alkyl, $C_{2-5}$ alkenyl and $C_{2-5}$ alkynyl; and $R^4$ is $C_{1-5}$ alkyl;

the method comprising the step of reacting a compound of formula (III) with a 2-ethylhexanoate salt:

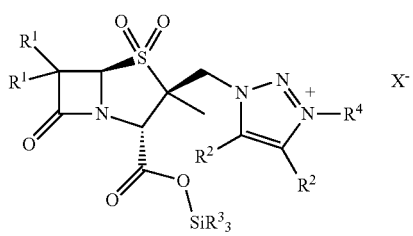

(III)

wherein X— is an anion and each $R^3$ is independently selected from the group consisting of $C_{1-10}$ hydrocarbyl and $C_{1-5}$ alkoxy.

9. A method according to claim 8 wherein the 2-ethylhexanoate salt is a metal 2-ethylhexanoate.

10. A method according to claim 9 wherein the metal is an alkali.

11. A method according to claim 8 wherein the compound of formula (III) is added to a solution of the 2-ethylhexanoate salt.

12. A method of forming a compound of formula (II)

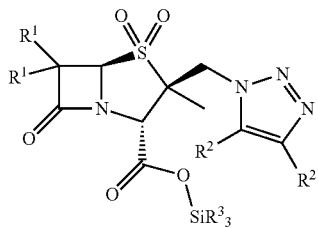

(II)

wherein $R^1$ in each occurrence is independently selected from H, halogen, amino, $C_{1-5}$ alkyl, $C_{2-5}$ alkenyl and $C_{2-5}$ alkynyl; $R^2$ in each occurrence is independently selected from H, halogen, amino, $C_{1-5}$ alkyl, $C_{2-5}$ alkenyl and $C_{2-5}$ alkynyl; and $R^3$ in each occurrence is independently selected from the group consisting of $C_{1-5}$ alkoxy and $C_{1-10}$ hydrocarbyl;

the method comprising the step of reacting a compound of formula (I) with less than a molar equivalent of a compound of formula (V)

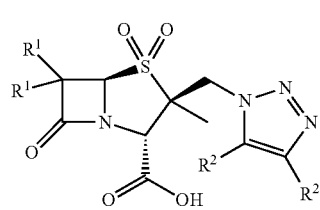

(I)

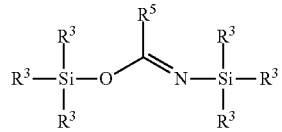

(V)

wherein $R^5$ is $C_{1-5}$ alkyl.

13. A method according to claim 12 wherein $R^3$ in each occurrence is independently selected from $C_{1-5}$ alkyl, $C_{1-5}$ alkoxy, phenyl, and phenyl-$C_{1-4}$ alkyl.

14. A method according to claim 1 wherein PG is a group of formula $SiR^3{}_3$ and wherein $R^3$ in each occurrence is independently selected from $C_{1-5}$ alkyl, $C_{1-5}$ alkoxy, phenyl, and phenyl-$C_{1-4}$ alkyl.

15. A method according to claim 14 wherein the compound of formula (IIa) has formula (2):

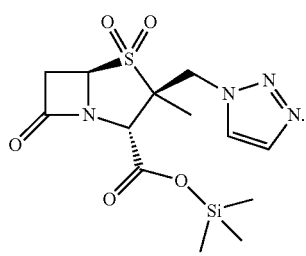

(2)

16. A method according to claim 12 wherein the compound of formula (I) has formula (1):

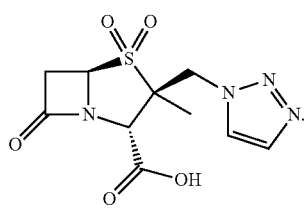

(1)

17. A method according to claim 12 wherein the compound of formula (V) is N,O-bis-trimethylsilylacetamide.

18. A method according to claim 8 wherein the compound of formula (IV) has formula (4):

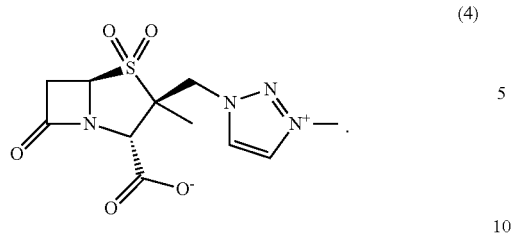
(4)
19. A method according to claim 8 wherein the compound of formula (III) has formula (3):
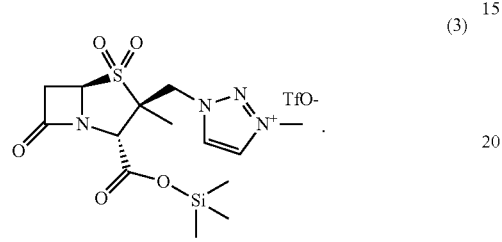
(3)
* * * * *